United States Patent [19]

Buening et al.

[11] Patent Number: 4,590,072
[45] Date of Patent: May 20, 1986

[54] LIVE VACCINE FOR BOVINE BABESIOSIS AND METHOD OF PREPARATION

[75] Inventors: Gerald M. Buening; Charles A. Carson, both of Columbia, Mo.

[73] Assignee: Curators of the University of Missouri, Columbia, Mo.

[21] Appl. No.: 663,844

[22] Filed: Oct. 31, 1984

Related U.S. Application Data

[63] Continuation of Ser. No. 438,641, Nov. 3, 1982, abandoned.

[51] Int. Cl.$^4$ ................... A61K 39/018; C12N 1/10
[52] U.S. Cl. ............................ 424/93; 435/258; 424/88
[58] Field of Search ................. 424/85-92, 424/93; 435/68, 258, 243

[56] References Cited

PUBLICATIONS

Wright, et al. (1981), *J. Protozool.* 28 (1): 118–120.
Callow (1977), *Adv. Exp. Med. Biol.*, 93: 121–149.
Erp, et al., 1978, Am. J. Trop. Med. Hyg. 27:1061–1064.
Levy et al., 1981, Cultivation of Babesia, pp. 207–223, in Ristic and Kreier, Babesiosis, Academic Press, Inc., N.Y.
Scheibel et al., 1979, Exp. Parasitol, 47:410–418.
Levy and Ristic (1980) Science 207: 1218–1220.
Smith, et al. (1979) Am. J. Vet. Res., vol. 40, No. 12: 1678–1682.
Smith et al. (1981) Science 212: 335–338.
Kuttler (1982) Am. J. Vet. Res. 43 (2): 281–284.
Callow, et al. (1979) Int. J. Parasitol 9: 333–338.

*Primary Examiner*—Blondel Hazel

[57] ABSTRACT

A live vaccine for bovine babesiosis comprises viable bovine erythrocytes parasitized with a cloned population of *Babesia bovis*, the clone strain being fast-growing, avirulent, and producing a mild but immunizing infection when administered. The vaccine is free of slow-growing virulent *B. bovis*. The clone strain used in the vaccine is prepared from a natural mixture of virulent and avirulent babesia by progressive dilution culturing to obtain cultures containing single parasites, propagating the single parasites under favorable conditions for growth, and selecting a fast-growing avirulent clone line for either in vitro or in vivo propagation to prepare the vaccines.

4 Claims, No Drawings

LIVE VACCINE FOR BOVINE BABESIOSIS AND METHOD OF PREPARATION

GRANT REFERENCE

The research which led to this invention was supported in part by a grant from the United States Department of Agriculture, Grant No. C-5-38065.

RELATED APPLICATION

This application is a continuation of our prior application Ser. No. 438,641, filed Nov. 3, 1982, and now abandoned.

BACKGROUND AND PRIOR ART

The field of this invention is vaccines for immunizing bovines against severe babesiosis infection. The invention is particularly concerned with vaccines for cattle prepared from the hemoparasite *Babesia bovis* (*B. bovis*). This invention has as its principal object the preparation of a live vaccine which is safer than the prior whole blood vaccines, and which will not make the immunized animal a carrier of virulent parasites.

Bovine babesiosis, caused by *B. bovis*, is one of the major constraints to cattle production in the tropics and subtropics. Premunition, or programmed infection of young cattle (viz. under 2 years) with infectious carrier blood, followed by monitoring and treatment if necessary, has been a commonly used protective procedure. See Gonzalez, et al., *Workshop on Hemoparasites (Anaplasmosis and Babesiosis)* 17–22 March, 1975, 147–151, CIAT-Cali, Columbia and Callow and Mellors, 1966, Aust. Vet. J., 42: 464–465. This method is effective but is is not without risk since virulent blood is used as inocula and pathogenic babesia are disseminated in the process.

An improvement on premunition utilizes an inoculum of bovine blood theoretically enriched for avirulent organisms. Callow et al., 1979, *Parasitol* 9: 333–338; Rowley, D. and Jenkins, C.R., 1962, Nature, 193: 151–154; Kahl, L.P. et al., 1982, 129: 1700–1705. This concept is based on the unproven assumption that field strains of babesia consist of a spectrum of parasites ranging from virulent (pathogenic) to avirulent (nonpathogenic). Apparently, rapid passage of field isolates through splenectomized calves sequentially enrich the population of organisms for the relatively avirulent, rapidly growing parasites. The excess of avirulent parasites stimulates the immune response in advance of the virulent parasites reestablishing their numbers—when this occurs the host's immune system is already capable of providing protection. In the host vaccinated in this manner, the babesia population "reverts to virulence" as the full range of organisms replicate in the intact host. Vaccinates become carriers from which virulent babesia can be transmitted by tick vectors. Aside from simple spread of the pathogen severe reactions may also occur, and care must be taken to modulate infections by chemotherapy when necessary.

More recently a subunit glycoprotein vaccine was produced using babesia surface coat material collected from bovine erythrocyte cell culture systems. Kuttler et al., 1982, *Am. J. Vet. Res.*, 43(2): 281–284. As with most subunit vaccines, the degree and length of protection may be less than that achieved using a live organism. In addition the elicited response is limited to the injected antigens as opposed to the wider breadth of response to a live parasite that can present an array of immunogens as it moves through a series of antigenic changes. Curnow, J.A., 1973, Aust. Vet. J., 49: 279–283.

SUMMARY OF INVENTION

This invention for the first time provides the vaccine art with a live parasite vaccine for safe immunization of bovines against severe babesiosis infection without making the immunized animal a carrier of virulent parasites. The vaccine comprises an aqueous carrier administerable to bovines containing bovine erythrocytes parasitized with a homogenous population of viable, fast-growing, avirulent *B. bovis* cloned from a single parasite. The vaccine is free of erythrocytes containing slow-growing virulent *B. bovis*. The cloned population is composed of a sufficient number of viable parasites to produce a mild babesiosis infection when administered to a non-immune bovine. An avirulent infection is characterized by a sharp temperature peak with the temperature returning to normal within 24 to 48 hours.

The vaccine is produced by an isolation and cloning procedure. The naturally derived culture is heterogeneous, containing parasites of varying growth rates from slow-growing to fast-growing. The growth of the parasites is promoted in cultures containing non-parasitized erythrocytes (normal red blood cells). The cultures are successively diluted until the penultimate cultures contain only one parasitized erythrocyte per culture well. Cultures are separately propagated to obtain populations of identical parasites. Clones are selected which have organisms with fast-growing, avirulent characteristics. A virulence is confirmed by determining the ability of the culture to cause only a mild infection when administered to a non-immune bovine. Cultures are then scaled up to produce the vaccine in dosage quantities. This can be done by in vitro culture using media containing non-parasitized, viable bovine erythrocytes. Alternatively, the culture can be propagated in vivo by inoculating an intact bovine and after parasitemia is observed harvesting the animal's blood for use in vaccine doses.

DETAILED DESCRIPTION iRBC = infected red blood cells (erythrocytes)
nRBC = normal red blood cells
PPE = percent parasitized erythrocytes The starting material for inoculating cell cultures for the present invention comprise bovine blood samples obtained from cattle or other bovines in which a severe babesiosis infection is in process. Cattle, oxen, and buffalo are bovines which are subject to the infection. It may be advisable to draw starting blood samples from bovines in the region in which the vaccine is to be used if strain differences prove to affect the vaccine's ability to stimulate protection. Since the *B. bovis* parasite is widespread in locations such as Mexico, Central and South America, Australia, and New Zealand production would be simplified if vaccines can be prepared of general utility.

The initial culture inoculum contains a small percent (viz. 0.1–1.0%) of parasitized erythrocytes (PPEs). Therefore, most of the red cells in these samples will be non-infected. The serial propagation and dilution procedure leading to the desired clone line for preparing the vaccine may be carried out with an aliquot of the whole blood sample. Preferably, however, the erythrocytes are sedimented and separated from most of the other constituents of the blood. Centrifugal separation procedures can be used. The separated RBC can be further purified by washing the cells with media 199, a buffered isotonic solution. Final suspension has a PCV of 5.0.

The mixed infected and normal RBC's may be propagated in standard 96-well culture plates using standard culture media. The wells should have flat bottoms to permit the erythrocytes to settle in layers of uniform depth beneath the surface of the culture medium. The culture system employed should be designed to promote parasite growth. The microaerophilous stationery phase system (MASP) developed by Levy and Ristic is suitable only if modifications are made. See Levy, et al., 1980 *Science,* 207: 1218-1220. The experimental work leading to the present invention has shown that the MASP conditions for *B. bovis* described by Levy and Ristic do not lead to satisfactory propagation of the parasite at dilutions below 0.1% PPE. With the Levy and Ristic conditions (5.0% $CO_2$ in air; fluid depth 6.2 mm) clones cannot be grown from individual parasites. By employing a modified atmosphere (2% $O_2$, 5% $CO_2$, 93% $N_2$) and a lower fluid level (4.0 infected mm), propagation of *B. bovis* at very low PPE concentrations down to a single infected cell can be obtained. The low PPE concentration propagation is also assisted by frequent removal and replacement of the culture medium above the settled mixture of parasitized and normal RBC's. Media is replaced once every 24 hours and cells subcultured every 72 hours by making 1:2 dilution with suspension (5.0 PCV) of nRBC has been found to be advantagous. Palmer, 1982, *Parasit.,* 84: 567–572. After counting the number of RBC in 1 μl and using the PPE determining the number of infected RBC per μl begin with a multiple of 10 iRBC and make serial 1:10 dilutions in culture media so that you isolate 1 iRBC in 200 μl of media. Divide this aliquot in 4 equal parts and dispense into 4 separate wells. In the final series of 4 wells only one contains a parasite—the others have none. To each of the final four wells nRBC are added to bring the PCV to 2.5%. Media is changed daily and an aliquot of normal RBC is added to bring the PCV up to 5.0% at 96 hours of incubation. Subcultures are made every 72 hours thereafter. If more than 1 well in 4 shows evidence of parasite growth it is evident that the corresponding penultimate well had more than one organism; thus this series is discarded. Cultures are separately propagated to obtain populations of identical parasites. Clones are selected which have fast-growing, avirulent characteristics. In the case of rapidly growing parasites the erythrocyte layer becomes dark in color after 9–12 days of incubation; at this time infected erythrocytes are readily found in Giemsa stained smears. Parasites considered slow growing take 17–20 days to cause erythrocyte darkening. At 9–12 days it is extremely difficult to find any infected red cells in Giemsa stained smears. Avirulence is confirmed by determining the ability of the culture to cause only a mild infection when administered to a non-immune bovine. Cultures are then scaled up to produce the vaccine in dosage quanities. This can be done by in vitro culture using media containing non-parasitized, viable bovine erythrocytes. Alternatively, the culture can be propagated in vivo by inoculating an intact bovine and after parasitemia is observed harvesting the animal's blood for use in vaccine doses.

Further, details of the culturing, serial dilution, and clone production procedures are set out below.

EXPERIMENTAL EXAMPLE

Cloning *B. bovis* in Bovine RBC Cell Culture:

Cultures are carried out at 37° C. in atmosphere containing 2% $O_2$, 5% $CO_2$ and 93% $N_2$. Fluid levels in 96 well culture plates ar 4.0 mm.

1. A 5 year old Holstein cow was inoculated intravenously with 2.0 ml of babesia infected erythrocytes (approximately 1.0 PPE) stored in liquid nitrogen until use. During the acute phase of the disease approximately 1.0 PPE blood was collected by venapuncture and defibrinated by shaking over glass beads. Fifty ml of blood was inoculated intravenously into a splenectomized calf. At the earliest signs of parasitemia blood was passed to the next splenectomized calf by intravenous inoculation. This procedure was repeated eight times. Blood from the ninth calf was collected by shaking over glass beads to defibrinate, centrifuged at 250 rpm and the buffy coat and plasma removed. The erythrocytes were suspended in culture media composed of 199 with Earle's salts and TES (25 mM/l).

2. Erythrocytes were diluted to form a 5.0 packed cell volume (PCV) using media 199 with Earle's salts and TES (25 mM/l). This is only one of several suitable media. Use 200 μl of RBC suspension per well in 96 well culture plates. These polystyrene plates have flat bottom wells that are 6.4 mm in diameter and 10 mm deep. All wells of the plate should contain fluid; if culture in only part of plate surround by water in remaining wells.

If cultures are started with frozen iRBC preparations—the 2.0 ml aliquot is thawed and mixed with 50.0 ml of Puck's saline; centrifuge at 3,000 rpm for 10 minutes art 4° C. Resuspend the pellet (packed RBC), approximately 0.1 ml in 1.0 ml of fresh culture media with 10.0% nRBC. Deposit into wells of culture plate—200 μl/well and incubate at 37.0° C.

3. For parasite propagation change media every 24 hours; subculture every 72 hours. When growth is detected by darkening of RBC or by making Giemsa stained blood smears mix 20 μl of 5.0% iRBC suspension added to 980 μl of 5.0% nRBC (1:50 dilution). Dispense into desired number of wells in 200 μl volumes.

(Note: if parasite growing rapidly use a higher dilution (eg 1:100) rather than 1:50; a 5.0% PCV should still be used).

4. Determine RBC/μl using a hemocytometer: count total RBC in both grids and divide by 2. Multiply by 2500 (dilution) factor to get RBC μl. Count PPE taking the average of 10 fields in each of 2 Giemsa stained blood smears. Multiply PPE x number of RBC/μl to arrive at number of infected RBC/μl.

5. Start serial dilutions only after "maternal" cultures go undisturbed (by not subculturing) for 48 hours. Begin with a multiple of 10 iRBC/μl. Deliver 20 μl of above suspension (you have $20 \times$iRBC/μl as total iRBC) into microtiter well and add 180 μl of media to bring volume to 200 μl. Make serial 1:10 dilutions with each well containing 200 μl so that the final well has 10 iRBC.

(Example—if you begin with $1.38 \times 10^6$ iRBC, for example, this will ultimately provide 1.38 organisms in the final dilution but it is necessary to isolate single parasites. Therefore, make a 1:13 dilution so that the beginning dilution is $1.0 \times 10^5$ organisms per 20 μl. Make 10-fold dilutions carrying out to the final well with 10 iRBC/200 μl.)

6. Divide this final well into 10 equal parts of 20 μl each—add 180 μl media to each well. This gives 1 iRBC in each well (theoretically). Divide contents of each well into 4 equal parts and dispense into 4 wells of 50 μl each; bring level up to 130 μl by adding nRBC suspension making a PCV of 2.5. (At this point, it would be expected to have growth in only 1 of each set of 4 wells. If otherwise, this step was started with more than 1 parasite in a single well so discard). Change media daily by replacing the supernate above the cell layer with fresh media. At 96 hours, remove 80 μl of supernate and add 80 μl of nRBC suspension to bring the PCV up to 5.0. Then continue to change media daily and subculture every 72 hours from contents of these "cloning wells". *Do not monitor the PPE in these wells to avoid sacrificing iRBCs.* Instead carry out the following:

7. To monitor parasite growth in "expendable" cultures—return to the serial dilution wells which preceded the steps where single parasites were finally isolated.

Divide the contents (180 μl) of the well initially containing $10^2$ parasites in half, dispense to separate wells and bring media level up to 135 μl with 2.5% nRBC in media. Carry out media changes and subculture exactly as in cloning set left undisturbed by PPE determinations.

Monitor wells in the entire original dilution plate for darkening of RBC layer—indicating parasite growth. Also examine Giemsa stained blood films for growth. As the increasing dilutions in this plate begin to exhibit growth, it can be expected that the undisturbed cloning wells will similarly begin showing evidence of growth. Therefore, closely observe the ultimate series of 4 wells for evidence of RBC darkening. At that time transfer the contents of the well showing evidence of growth (verify by blood smears) to a separate culture plate. Repeat the dilution (cloning) process twice to obtain secondary and tertiary clones. At this point there is nearly a 95.0% certainty that the tertiary clone originated from a single parasite, which is the objective of the entire procedure. The population of parasites now present should be a homogeneous one.

Clones develop into measurably infected bovine erythrocyte populations in 9–20 days. Using the foregoing procedure, three clones were isolated, and each had a characteristic rate of growth during the cloning process, designated as fast, slow or intermediate. The rapidly growing parasites turn the erythrocytes dark in color in 9 to 12 days; at this time organisms are readily found in Giemsa stained smears. Parasites termed slow growing take 17 to 20 days to produce darkening of the erythrocyte layer detectable by the naked eye. In these cultures it is still virtually impossible to find infected erythrocytes in cultures examined via Giemsa stained smears after 9 to 12 days in culture. It is postulated that the fast growing organisms will be the more avirulent, and therefore, useful as a vaccine against bovine babesiosis. Preliminary trials have tended to confirm this.

By the foregoing standard, the fast-growing clone had a growth rate of 9 days (starting with 1.0 iRBC and increasing to 2.0–3.0 PPE), the slow-growing clone had a growth rate of 17 days, and the intermediate growth rate clone had a growth rate of 15 days. The fast-growing clone, designated clone line MO-3, was selected as providing a preferred strain of identical parasite population for use in preparing the vaccines. This clone line MO-3 has been deposited with the American Type Culture Collection, Rockville, Md., and has been assigned Deposit No. 40056. This deposit was in accordance with the provisions of the Budapest Treaty.

The deposited culture (MO-3) is in the form of erythrocytes in 10.0% (V/V) polyvinylpyrrolidone (PVP) that were frozen to minus 70° C. at a freezing rate of 20° C./min. Approximately 10.0% of the erythrocytes are parasitized with the clone strain. The parasites have the typical morphology of *B. bovis* parasites. The deposited culture is free from any virulent slow-growing *B. bovis*. When administered to cattle in amount sufficient to cause a babesiosis infection, only a mild infection will result. Shortly after the onset of the infection, the animal's temperature will rise to about 104.0° F., but will not remain elevated, as it does with severe babesiosis infection. Within 24 to 48 hours after the fever peak is noted, the temperature will fall toward normal, and within 12 hours will reach the normal temperature level of 101.5° to 102.5° F. Clinically, mild babesiosis infections are readily distinguishable from severe infections. Virulent *B. bovis* causes fever (to 106.0° F.), lethargy, inappetance, anemia, jaundice, central nervous signs and usually death. A virulent babesia produce only a transient fever (from 103.0° to 105.0° F.).

PREPARATION AND ADMINISTRATION OF VACCINES

A. In vitro Cultivation

Blood collected from a bovine acutely or chronically affected by babesiosis (*B. bovis*); from a source without a history of leukemia or other blood parasites, can serve as the culture "starter". Erythrocytes may be sedimented by centrifugation, the supernate and buffy coat removed and the red cells washed three times in tissue culture media—for this purpose media 199 with Earle's salts (K.C. Biological, Lenexa, KS) can be used. The erythrocytes are diluted as described in the Experimental Example and cultures set in large glass or polystyrene vessels using the specific atmosphere gas mixture previously described. Fluid levels in the vessel should be 4.0 mm. When the erythrocytes begin to darken or smaller sample vessels are opened and Giemsa stained slides show infected RBC a 5.0% suspension of iRBC is diluted 1:50 or 1:100 with a 5.0% suspension of nRBC. Change media every 24 hours and subculture every 72 hours by diluting culture 1:2 with nRBC suspension. Typically cultures started with a 0.1 to 1.0 PPE will reach 10.0 PPE in 72 hours or less.

Cultures may be harvested every 72 hours and preserved in 10.0% PVP (V/V) followed by freezing at the rate of 20° C./min to −70° C. and kept frozen in liquid nitrogen until used. Aliquots of vaccine should contain $1 \times 10^5$ parasitized erythrocytes/dose.

B. In vivo Cultivation

A bovine free of hemotropic or other diseases and from a herd known to be free of bovine leukosis is splenectomized. Two weeks after splenectomy Giemsa stained blood films must be examined to determine the presence of eperythrozoon. If these are visible the animal should receive two doses of neoarsphenamine (1 gm/100 lbs) with a one week interval to clear eperythrozoon if present. Allow 10 days before infecting with babesia. A single vial of *B. bovis* infected erythrocytes from cell culture, containing approximately $1 \times 10^5$ infected RBC is injected into the animal by intravenous inoculation. Monitor the presence of parasitemia via daily Giemsa stained blood films and when the PPE seems to have peaked exsanguinate the animal into collection vessels while shaking over glass beads to defibrinate. The blood can then be dispensed into vials for freezing using PVP as a cryoprotectant, frozen at the controlled rate and stored in liquid nitrogen. Each vial should contain approximately $1 \times 10^5$ infected RBC.

The in vitro vaccine prepared as described above can be administered to cattle by single subcutaneous injection. Extra care should be taken to monitor any clinical signs that may occur when used in expensive purebred cattle. The observation period should last for 14 days. In the event of clinical evidence of babesiosis chemotherapy should be initiated.

We claim:

1. The method of preparing a live parasite vaccine for safe immunization of bovines against severe babesiosis infection, comprising the sequence of steps of:
   (a) subjecting cultures of a mixed parasite population of viable *Babesia bovis* to a series of in vitro propagations in a cell culture medium, said mixed population including both slow-growing virulent parasites and fast-growing avirulent parasites, said parasites being contained in parasitized bovine erthrocytes in admixture with non-parasitized bovine erythrocytes;
   (b) successively diluting the mixed cultures during said propagations until the final cultures contain only a single parasite per culture;
   (c) separately propagating each of said single parasites in non-parasitized bovine erythrocytes under conditions effective for single parasite propagation to obtain a series of clone cultures, each clone culture containing only a homogeneous parasite population;
   (d) selecting from said series a clone culture in which the parasite therein has a fast-growing characteristic;
   (e) confirming that the selected fast-growing parasite has an avirulent character by administering a sample of the parasite to a non-immune bovine, and determining that the culture produces a mild infection characterized by a sharp temperature peak with the temperature falling toward normal within 24 to 48 hours after the administration; and, thereafter,
   (f) propagating the confirmed avirulent clone parasite to produce vaccine doses thereof.

2. The method of claim 1 in which said vaccine is for administration to cattle, and said bovine erythrocytes are cattle erthrocytes.

3. The method of claim 1 in which step (f) is carried out in vitro using said non-parasitized erythrocytes in a culture medium substantially free of other constituents of blood.

4. The method of claim 1 in which said vaccine is for administration to cattle, said bovine erythrocytes are cattle erythrocytes, and step (f) is carried out in vitro using non-parasitized erythrocytes in a culture medium free of other constituents of blood.

* * * * *